United States Patent
Cestari Soto et al.

(10) Patent No.: US 10,016,331 B2
(45) Date of Patent: Jul. 10, 2018

(54) ARTICULATION WITH CONTROLLABLE STIFFNESS AND FORCE-MEASURING DEVICE

(71) Applicants: CONSEJO SUPERIOR DE INVESTIGACIONES CIENTIFICAS (CSIC), Madrid (ES); UNIVERSIDAD POLITECNICA DE MADRID, Madrid (ES)

(72) Inventors: Manuel Javier Cestari Soto, Madrid (ES); Daniel Sanz Merodio, Madrid (ES); Elena Garcia Armada, Madrid (ES)

(73) Assignees: CONSEJO SUPERIOR DE INVESTIGACIONES CIENTIFICAS (CSIC), Madrid (ES); UNIVERSIDAD POLITECNICA DE MADRID, Madrid (ES)

( * ) Notice: Subject to any disclaimer, the term of this patent is extended or adjusted under 35 U.S.C. 154(b) by 266 days.

(21) Appl. No.: 14/896,814

(22) PCT Filed: May 23, 2014

(86) PCT No.: PCT/ES2014/070422
§ 371 (c)(1),
(2) Date: Dec. 8, 2015

(87) PCT Pub. No.: WO2014/198979
PCT Pub. Date: Dec. 18, 2014

(65) Prior Publication Data
US 2016/0136031 A1 May 19, 2016

(30) Foreign Application Priority Data
Jun. 13, 2013 (ES) .................................. 201330882

(51) Int. Cl.
*A61H 3/00* (2006.01)
*A61F 2/76* (2006.01)
(Continued)

(52) U.S. Cl.
CPC ................. *A61H 3/00* (2013.01); *A61F 2/50* (2013.01); *A61F 2/76* (2013.01); *B25J 9/1694* (2013.01);
(Continued)

(58) Field of Classification Search
CPC ...... A61H 3/00; A61F 2/76; A61F 2/50; B25J 17/00
(Continued)

(56) References Cited

U.S. PATENT DOCUMENTS

| 5,650,704 | A  | * | 7/1997 | Pratt  | .......................... B25J 9/10 318/560 |
| 7,109,679 | B2 | * | 9/2006 | Edson  | .................. G05B 19/404 318/611 |
| 9,091,306 | B2 | * | 7/2015 | Orita  | ....................... F16D 28/00 |

* cited by examiner

Primary Examiner — Harshad R Patel
Assistant Examiner — Jamel Williams
(74) Attorney, Agent, or Firm — Lucas & Mercanti, LLP

(57) ABSTRACT

The subject matter of the invention is an articulation (1) with controllable stiffness and a force-measuring system, comprising a first device (20) that comprises a frame (4) having a curved face and connected to a first motor element (2), the first device (20) regulating the position of the articulation (1), and a second device (22) that regulates the stiffness of the articulation (1) and comprises a thrust element (15), the movement (D) of which determines the pre-compression of a resistive element (11) and thus the stiffness of the articulation (1); the first motor element (2) causes the frame (4) to rotate such that a wheel (8) of the second device (22) rolls on the curved face of the frame (4), causing the resistive element (11) to be compressed (C) via a transmission rod (7)

(Continued)

associated with the wheel (8) and with the resistive element (11).

8 Claims, 6 Drawing Sheets

(51) Int. Cl.
*B25J 17/00* (2006.01)
*B25J 19/06* (2006.01)
*A61F 2/50* (2006.01)
*B25J 9/16* (2006.01)

(52) U.S. Cl.
CPC ............. *B25J 17/00* (2013.01); *B25J 19/068* (2013.01); *A61F 2002/503* (2013.01); *A61F 2002/5073* (2013.01); *A61F 2002/7635* (2013.01)

(58) Field of Classification Search
USPC ........................ 73/862.381; 318/611; 901/23
See application file for complete search history.

ARTICULATION WITH CONTROLLABLE STIFFNESS AND FORCE-MEASURING DEVICE

OBJECT OF THE INVENTION

The articulation object of the invention is part of the mechanical engineering sector, and can be used particularly in the industrial field of manufacturing orthopaedic and prosthetic devices or mobility aids for elderly or disabled people, in the field of rehabilitation, increasing power exoskeletons and walking robotics.

TECHNICAL PROBLEM TO BE SOLVED AND BACKGROUND OF THE INVENTION

Both animals and human beings are able to have a wide range of stable movements in different environments with unpredictable obstacles. For this, a dynamic control of the stiffness of articulations to allow for their adaptation to these changes is crucial. Human articulations are groups of muscles that enable the control of both the stiffness of the articulation and its position, thus allowing for a wide variety of modes of locomotion and simultaneous adaptation to different ground with acceptable energy efforts. Currently, a large number of devices associated with locomotion such as prostheses, orthoses, exoskeletons and walking robots are trying to integrate devices that emulate the functioning of the natural muscles in order to obtain movements with better energy efficiency, adaptability, and to increase security in the human-robot interaction.

In the search for obtaining articulations, whose behaviour is similar to human ones and which enable taking advantage of the natural dynamics of the movements and the configuration of the articulation characteristics facing the different requirements of the motion, many designs and research are being oriented to the development of motorised articulations, which are capable of adapting to obstacles of an unknown environment and have energy storage capacity to reduce the energy efforts of locomotion.

Document U.S. Pat. No. 5,650,704 presents one of the first designs that incorporated an element providing both adaptation and shock absorption capacity to the actuating system. This actuator makes use of elastic elements connected in series to the power drive train and not only allows to attribute some of the characteristics of the natural muscle to an electric actuator, but also allows to control the force exerted on the load by the operator. The main disadvantage of this mechanism is that the stiffness of the system is fixed, so it is restricted to an energetically optimal operating speed and load.

Other designs have focused on the modification of the stiffness of the articulation with the purposes of energy optimisation and utilisation of the locomotion dynamics. The document "P. Cherelle, V. Grosu, P. Beyl, A. Mathys, R. Van Ham, M. Van Damme, B. Vanderborght and D. Lefeber. '*The MACCEPA Actuation System as Torque Actuator in the Gait Rehabilitation Robot ALTACRO*' International Conference on Biomedical Robotics and Biomechatronics (2010)" presents the incorporation of a mechanically adjustable actuator to a rehabilitation exoskeleton, such an actuator allowing a safe interaction between the user and the machine and meeting the typical power requirements in rehabilitation of human locomotion. The document EP1726412A1 presents the base actuator used in the exoskeleton mentioned above, with the help of elastic elements and a motor responsible for variation in position and another one for the stiffness of the system, both characteristics being controlled independently. This design is aimed at rehabilitation and not strictly at a continuous variation of the parameters of the articulation to achieve greater locomotion efficiency.

The document "Sebastian Wolf and Gerd Hirzinger" *A New Variable Stiffness Design: Matching Requirements of the Next Robot Generation* 2008 IEEE International Conference on Robotics and Automation", describes an articulation for a robotic arm, in which a parallel arrangement allows the variation of the stiffness of the articulation, making it adaptable. In addition to the motor that moves the articulation, an additional motor, responsible for the suitability of the system, is necessary, with the characteristic that both operate in antagonistic way, what represents an increase in energy consumption. Even so, by taking advantage of the movement dynamics and by the appropriate articulation stiffness variation, a reduction of the net energy for the operation cycle is obtained. The measurement of the force/torque in the articulation is obtained through the incorporation of an external torque sensor between the actuator and the load.

Document WO/2012/038931 A1 presents several configurations mainly developed by the Italian Institute of Technology (IIT). Like the above-mentioned designs, they use 2 motors to independently operate on the position of the articulation and its stiffness, with the novelty of requiring lower energy associated with the variation of stiffness because it does not operate in the same direction of action as the elements that move the articulation. The document "Amir Jafari, Nikos G. Tsagarakis and Darwin G. Caldwell. 'AwAS-II: *A New Actuator with Adjustable Stiffness based on the Novel Principle of Adaptable Pivot point and Variable Lever ratio*' 2011 IEEE International Conference on Robotics and Automation", presents an actuator of this type, whose final implementation is expected to be in an exoskeleton knee articulation. However, the arrangement of the elements in this motorised articulation results in a system of still excessive dimensions for use in exoskeletons, mainly by the parallel arrangement of most of the parts of the device and the use of an external torque sensor between the actuator and the load.

All the actuated articulations that have controllable stiffness are characterised in that they typically include an element of measurement of the torque generated at the articulation, which is connected in parallel with the articulation actuating system. By making use of these elements traditionally connected in parallel with the structure, a considerable increase in the volume of the articulation is obtained, which is not at all desirable for use in exoskeletons for locomotion aid because what is of interest is to minimise its volume. This will be apparent in the designs of document WO/2012/038931 A1.

DESCRIPTION OF THE INVENTION

The object of the invention is an articulation with controllable stiffness and a force measuring system, comprising a first device that performs the adjustment of the position of the articulation and a second device that regulates the articulation stiffness.

The first device comprises a frame connected to a first motor element and the second device also serves as an anchorage for the first device to the articulation.

The second device comprises a coupling body, a resistive element, which can be of elastic, shock absorbing type or a combination thereof, a transmission rod attached at one end to the resistive element and comprising a wheel at the opposite end, a thrust element with a threaded spindle through it, on which the resistive element rests, and a second motor attached to the spindle which provides a displacement to the thrust element by a rotation of said spindle.

The displacement of the thrust element determines a pre-compression of the resistive element, thus determining the articulation stiffness, while the first motor element provides a rotation to the frame of the first device, wherein the frame has a curved face, such that, with the rotation of the frame, the wheel of the second device rolls on the curved face of the frame, and the transmission rod associated with said wheel causes a compression of the resistive element of the second device, so this compression determines a force developed by the resistive element known as $F_{thrust}$.

The second device of the articulation object of the invention comprises a rotational measurement element connected to the second motor, said rotational measuring element counting the revolutions of the shaft of the second motor, so that the displacement of the thrust element is known by performing a conversion of the revolutions of the second motor and of the pitch of the spindle, where a second motor revolution is equivalent to the spindle pitch in the linear displacement of the thrust element associated with the spindle, so that the displacement of the thrust element is known by the relation:

Displacement=Revolutions·Pitch.

The second device of the articulation object of the invention comprises an element of linear measurement and a graduated scale attached to the transmission rod, such that compression experienced by the resistive element associated to the rotation of the frame is known through the element of linear measurement, which measures the displacement of the transmission rod on the graduated scale.

The articulation object of the invention takes advantage of the resistive element associated with its stiffness for obtaining the measurement of the torque generated at the articulation through the relation:

Torque=$\vec{b} \times \vec{Fn}$, which is converted to Torque=
$\overline{b}Fn\sin(\varphi^*)$ where
$\vec{b}$ is a vector that represents a distance between an articulation rotation axis (O) and a point of contact of the frame (4) with the wheel (8), and
Fn is the contact force between the surfaces of the frame (4) and (8) wheel in the radial direction of the wheel (8);
$\varphi^*$ is an angle between the vector $\vec{b}$ and the vector $\vec{Fn}$,
The value of $\overline{b}$ is obtained from the relation: $\overline{b}=\sqrt{\overline{OB}^2+R^2-2\cdot\overline{OB}\cdot R \cdot \cos(\beta)}$ $\beta$ being the complementary angle which defines the inclination of the vector of the contact force $\vec{Fn}$, and is obtained by the relation $$\beta = \overline{OA} \cdot \frac{\sin\theta}{\overline{BA}},$$

$\theta$ being the deflection angle.
The value of $\theta$ is obtained from the expression $$\theta = \mathrm{acos}\left[\frac{\overline{OB}^2 + \overline{OA}^2 - \overline{BA}^2}{2\overline{OB}\cdot\overline{OA}}\right],$$

where
$\overline{OB}$: is the distance from the articulation rotation axis (O) to the centre of curvature of the curved face of the frame (B);
$\overline{OA}$: is the distance from the articulation rotation axis (O) to the centre of the wheel (A);
$\overline{BA}$: is the distance from the centre of the curvature of the frame (B) to the centre of the wheel (A).

The value of $\varphi^*$ is obtained from the expression $\varphi^*=\beta+\varphi+\theta$, where $$\varphi = \mathrm{arccos}\left[\frac{\overline{b}^2 + \overline{OA}^{2-r^2}}{2\cdot \overline{b}\cdot \overline{OA}}\right]$$

The value of Fn is obtained from the expression Fn=$F_{thrust}\cos(\varphi)$

The value of $F_{thrust}$ is obtained from the expression $F_{thrust}$=K·C+A·Vel, where K is the constant which is characteristic of the resistive element (11), C is the compression of the resistive element (11), A is the shock absorption constant of the resistive element (11) and Vel is the velocity of compression of the resistive element (11) when the settings of the system contain them.

The first device of the articulation object of the invention comprises, apart from the frame and the first motor element, a reducer that has a stationary part and an output, the frame being attached to the stationary part of the reducer; a first disc connected to the output of the regulator; and a second disc connected to the frame, in which the first disc is inserted.

The coupling body of the second device of the articulation object of the invention comprises guide channels, which guide the movement of the thrust element, and through-holes, the transmission rod passing through these through-holes.

In the articulation with controllable stiffness and force measuring device object of the invention, the thrust element is a flat piece, whose movement is limited by the guide channels of the coupling body of the second device.

DESCRIPTION OF THE FIGURES

In order to complete the description and to help achieve a better understanding of the features of the invention, this patent specification is accompanied by a set of drawings as an integral part, wherein the following has been represented merely for illustrative and non-limiting purpose.

Below is a list of the elements represented in the figures that make up the invention:

1.—articulation, 2.—first motor element, 3.—reducer, 4.—frame, 5.—second disc, 6.—first disc, 7.—transmission rod, 8.—wheel, 9.—linear measurement element, 10.—graduated scale, 11.—resistive element, 12.—second motor element, 13.—coupling body, 14.—guide channels, 15.—thrust element, 16.—spindle, 17.—rotational measurement element, 18.—first body, 19.—second body, 20.—first device, 21.—through-hole, 22.—second device; O.—rotation axis of the articulation; A.—center of the wheel; B.—centre of curvature of the frame; C.—compression of the resistive element, D.—Displacement of the thrust element. K.—constant characteristic of the resistive element, A.—shock absorption constant of the resistive element.

DESCRIPTION OF A PREFERRED EMBODIMENT OF THE INVENTION

In view of the above mentioned and with reference to the numbering adopted in the figures, the object of the invention is an articulation (1) with controllable stiffness, which allows to control the automatic rotational motion of a first body (18) and a second body (19), which are attached to a pivot point and simultaneously allow to control the stiffness of said rotational motion.

The articulation (1) object of the invention has the ability to regulate its position and stiffness independently, and for this regulation it uses two devices (20, 22) arranged in series along the said articulation (1) so that the presence of the two devices (20, 22) does not cause an increase in total volume with respect to an articulation (1) that does not have said devices (20, 22) for regulating the position and stiffness that the articulation (1), object of the invention, has. By these regulations the articulation (1) object of the invention allows the measurement of the force developed in the articulation (1) through the devices regulating the position and stiffness of the articulation (1).

Figure 1:
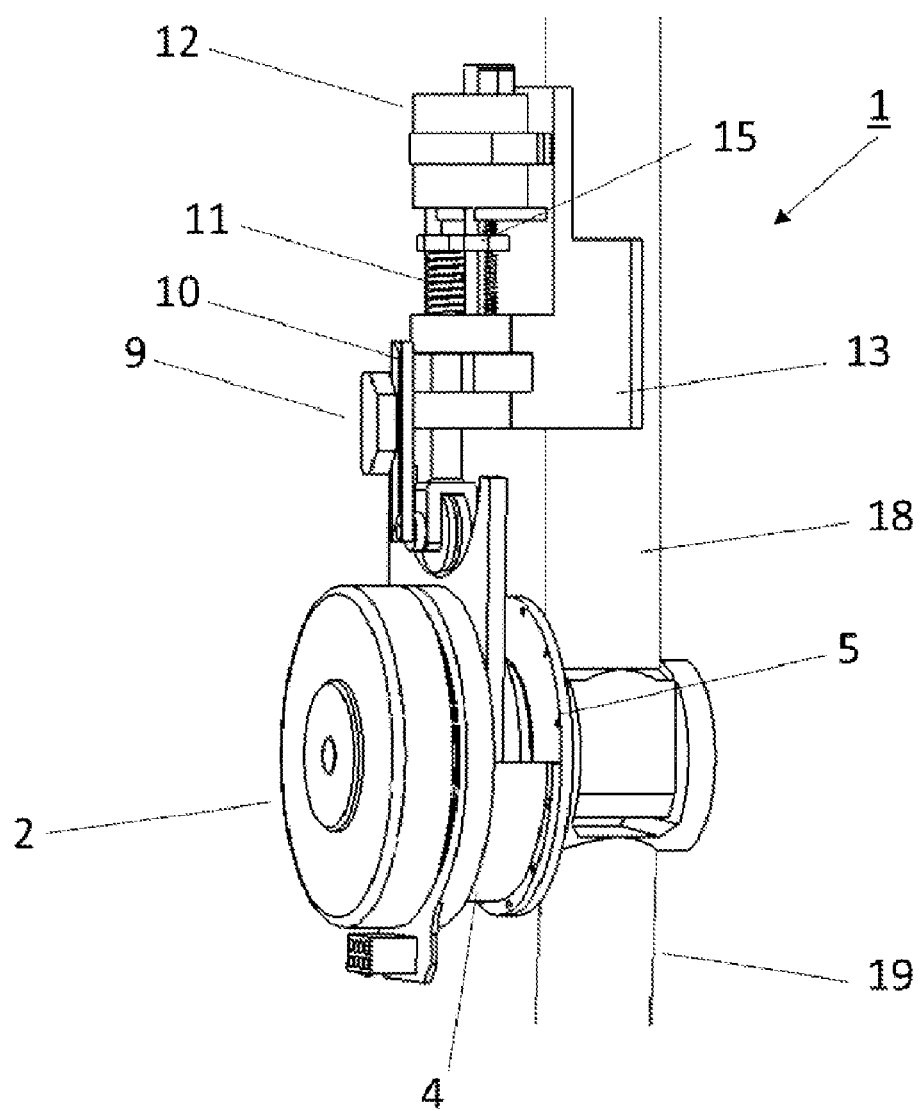
FIG. 1 shows an elevation view of an embodiment of the articulation object of the invention.
Figure 2:
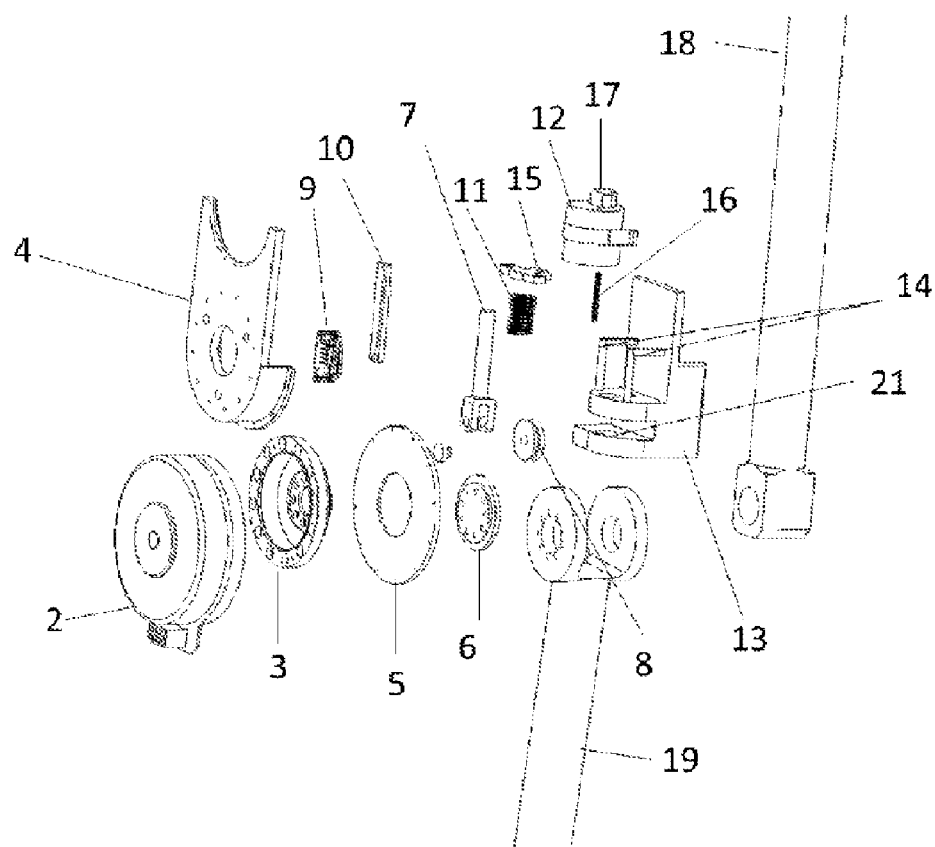
FIG. 2 shows an exploded view of an embodiment of the articulation object of the invention.
Figure 6:
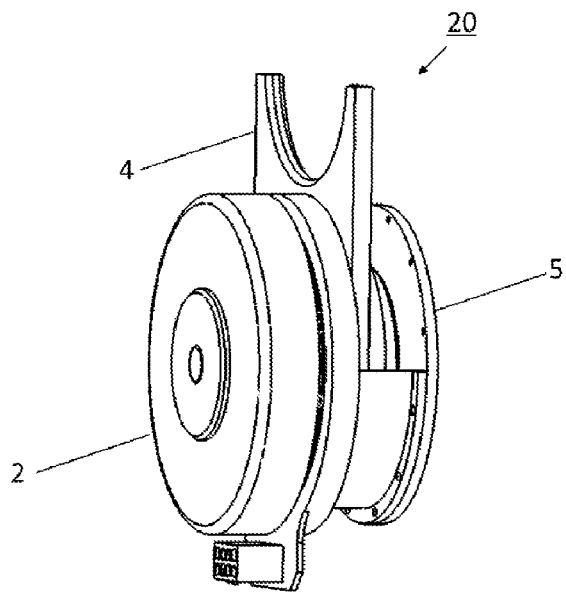
FIG. 6 shows an elevation view of the elements of the position variation.

The articulation (1) object of the invention (which can be seen in FIGS. 1 and 2) comprises a first device (20) (which can be seen in FIG. 6) which performs the regulation of the position of the articulation (1), this first device (20) comprising the following elements:

a frame (4) connected to a first motor element (2), which has a curved face;
a reducer (3) having a stationary part and an output part (4), the frame being connected to the stationary part of the reducer (3);
a first disc (6) connected to the reducer output (3);
a second disk (5), connected to the frame (4), into which the first disc (6) is inserted.

The joining of the pieces that make up this first device (20) is made by nuts and bolts.

This first device (20) (which can be seen in FIG. 6) connects to the first body (18) at the point where the first body (18) is pivotally connected relative to the second body (19).

Figure 7:
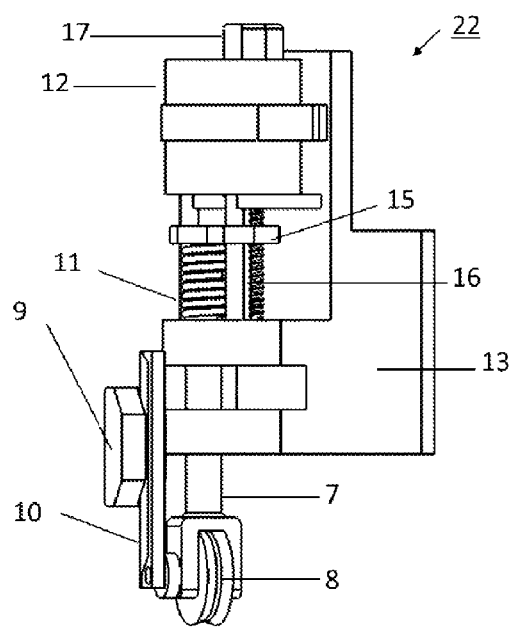
FIG. 7 shows an elevation view of the elements for the fixation and control of the stiffness.
Figure 8:
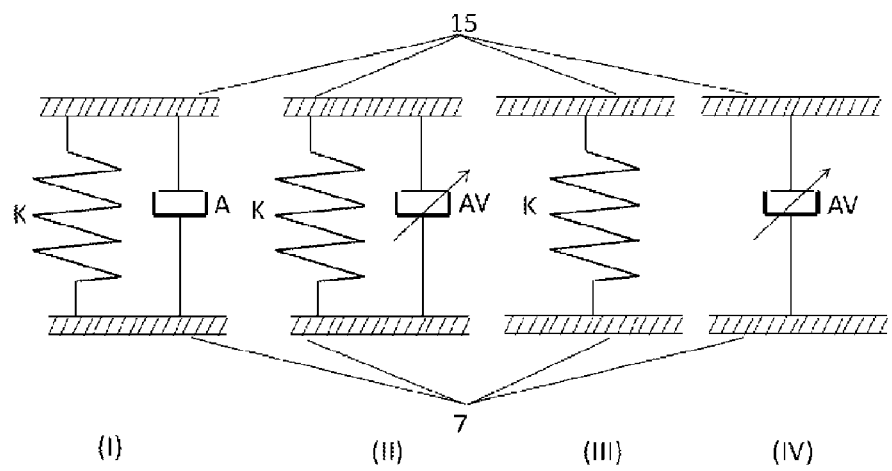
FIG. 8 shows four configurations of the element resistive, i.e., elastic cushioned stationary, elastic cushioned variable, only elastic or only cushioned and adjustable configuration.

The second device (22) is a device that regulates the stiffness of the articulation (1) (which can be seen in FIG. 7) and acts as anchorage for the first device (20). The second device (22) comprises the following elements:

a coupling body (13) comprising guide channels (14) and through-holes (21), with the coupling body (13) embracing the first body (18);
a resistive element (11) with different configurations (which can be seen in FIG. 8);
a transmission rod (7) moving along the inside of the through-holes (21) of the coupling body (13), the transmission rod (7) being connected at one end to the resistive element (11) and comprising a wheel (8) at the opposite end, with the wheel (8) being in contact with the curved face of the frame (4) of the first device (20);
a thrust element (15) which is moved guided by the guide channels (14) of the coupling body (13) and contacts the resistive element (11);
a second motor (12) which changes the position of the thrust element (15) through a threaded spindle (16) on said thrust element (15);
a linear measuring element (9) which is fixed in the coupling body (13);
a graduated scale (10) connected to the transmission rod (7) moving inside the linear measurement element (9).

The element (11) is formed by the combination of two elements: an elastic element (having a characteristic constant K) and a shock absorber element (with a shock absorption constant A) and possible combinations thereof. Furthermore, the shock absorber element has two options: being a stationary shock absorber or a variable shock absorber.

In one embodiment of the invention, the thrust element (15) is a flat piece that is guided within the guide channels (14) of the coupling body (13). On this flat piece, the resistive element (11) rests, so that through the displacement of the thrust element (15) a pre-compression of the aforementioned resistive element (11) can be performed. Also the transmission rod (7) is attached to this resistive element (11).

The second motor (12) modifies, through the spindle (16), the position of the thrust element (15) that is moved over the guide channels (14). By varying the position of the thrust element (15) the pre-compression of the resistive element (11) of the second device (22) is modified. Since this thrust element (15) is the element on which the resistive element (11) rests, the position in which the thrust element (15) is determines the pre-compression of the aforementioned resistive element (11).

Figure 5:
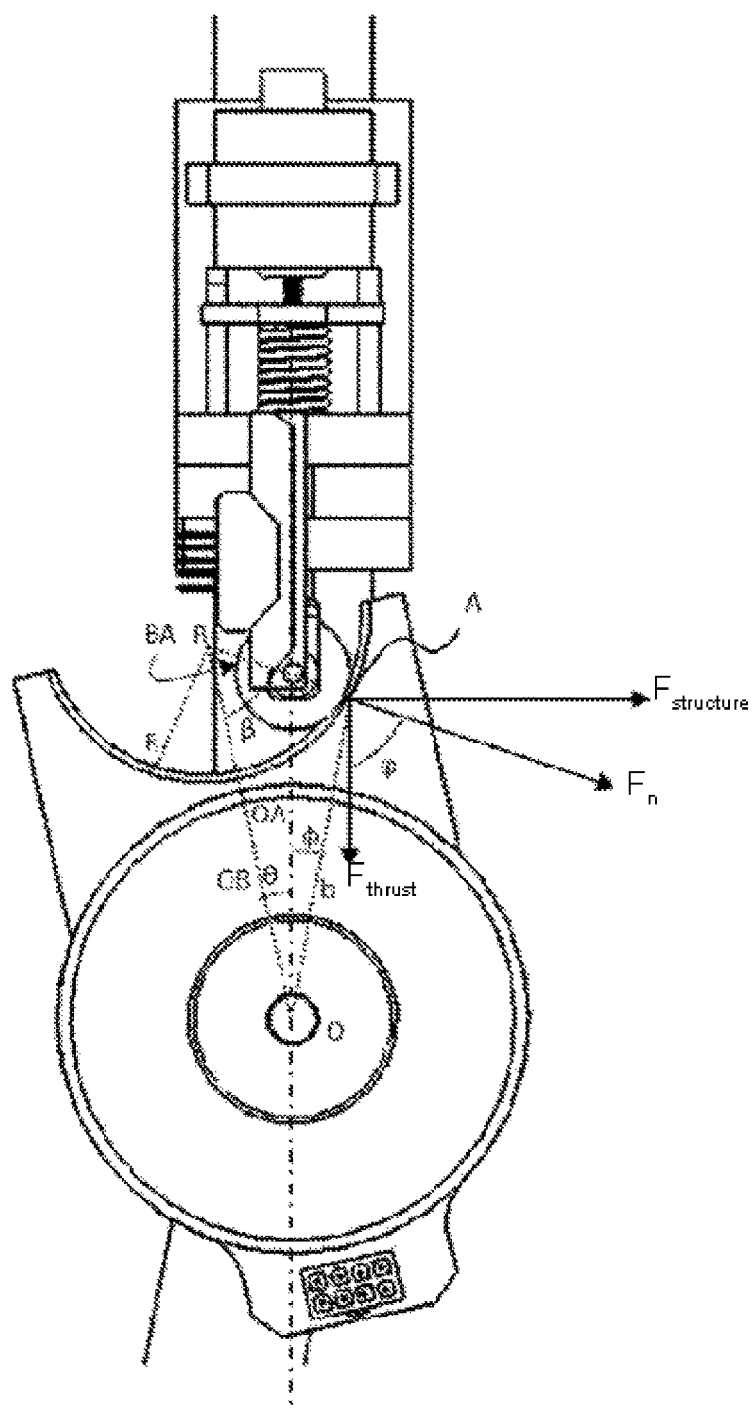
FIG. 5 shows the articulation by evidencing the influence of the deflection and compression of the resistive element in the contact angles, where the geometric relations that allow to obtain the reaction force Fn as a function of the "vertical" component $F_{thrust}$ can be seen.

As the resistive element (11) is associated to the thrust force of the transmission (7) and the wheel (8) contacts the frame (4), it is the pre-compression of the resistive element (11), together with the values of the constants K and A of the resistive element (11) that determine the stiffness of the articulation (which can be seen in FIG. 5).

The initial pre-compression of the resistive element (11) is known thanks to a rotational measurement element (17) connected to the second motor (12). Said rotational measurement element (17) is a rotational encoder that allows to know the revolutions of the second motor (12) when said second motor (12) is moving. In order to know the initial pre-compression, a conversion of the revolutions of the second motor (11) and of the pitch of the spindle (16) must be performed, a revolution of the second motor (12) being equivalent to the pitch of the spindle (16) in the linear displacement of the mentioned spindle (16).

The conversion of the revolutions of the second motor (12) and the pitch of the spindle (16) to the linear displacement of the thrust element (15), is such that once the pitch of the spindle (16) and the number of revolutions made by the second motor (12) are known, the linear displacement of the thrust element (15) connected to the spindle (16) is known through the relation:

$$Displacement = N \cdot P$$

Where:
D: Displacement of the thrust element (15),
N: N° of revolutions of the second motor (12),
P: Pitch of the spindle (16).

The linear measurement element (9) in the preferred embodiment of the invention is a linear encoder, which in combination with the graduated scale (10) performs the measurement of the linear displacement of the transmission rod (7) in the graduated scale (10).

Figure 3:
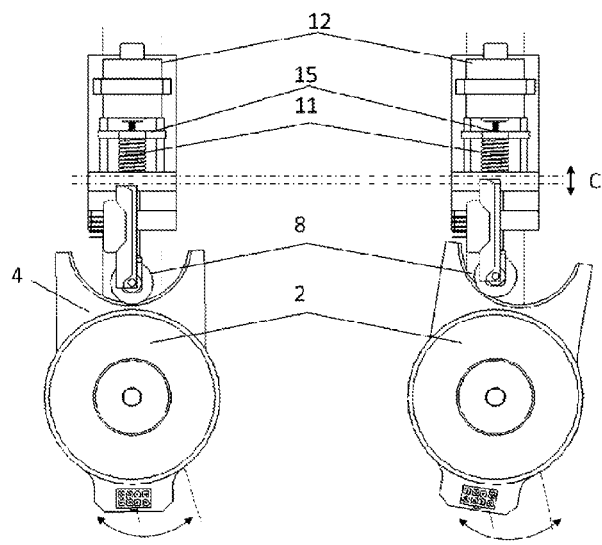
FIG. 3 shows a front view of the articulation in neutral position and with deflection.

With the thrust element (15) fixed at a position, i.e., with the stiffness of the articulation (1) already fixed, it is the shape of the frame (4) of the first device (20) that causes a compression of the resistive element (11) of the second device (22) in the presence of deflection at the articulation (1) (see FIG. 3).

The geometric shape of the frame (4) contributes to the measurement of torque and to a mechanical locking that allows a maximum of deflection to be adjusted as a function of the geometry of the frame (4).

The second device (22) acts as an anchorage of the first device (20), while through the contact of the wheel (8) on the curved face of the frame (4), the wheel (8) applies a pressure corresponding to the force transmitted by the transmission rod (7) attached to the resistive element (11), the transmission rod (7) moving inside the through-holes (21).

The second device (22) can modify its geometry, thus allowing a greater or lesser deflection in the articulation (1) (as shown in FIG. 3). The torque of the articulation (1) can be measured by the trigonometric relations between the elements of the second device (22) for force control in the articulation (1).

Figure 4:
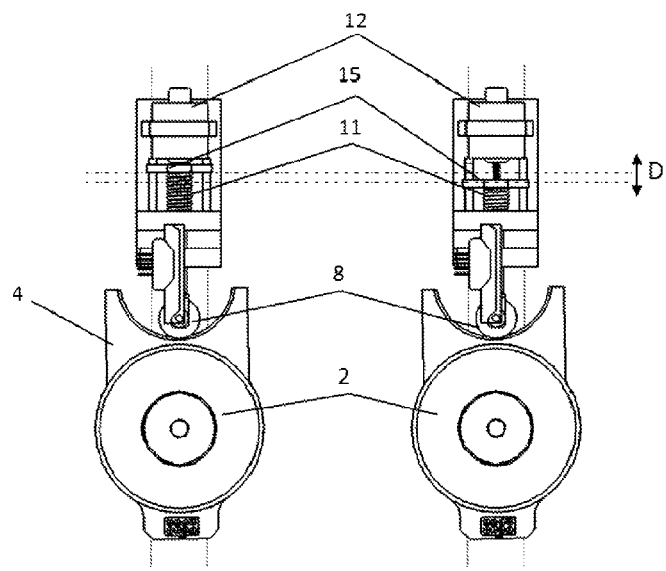
FIG. 4 shows a front view of the articulation with different pre-compression.

When the first motor element (2) of the first device (20) applies a torque and the frame (4) performs a rotational movement, the wheel (8) of the second device (22) rolls on the curved face of said frame (4), thus transmitting a reaction along the transmission rod (7), which is connected to the resistive element (11). The resistive element (11), as a function of its pre-compression, exerts more or less resistance to deformation, on which the deflection of the articulation depends (see FIGS. 3 and 4).

Deflection means a rotation in the frame (4) and therefore in the first device (20), without the need of any variation occurring in the position of the articulation (1), or the opposite case, i.e. in which the articulation (1) allows a rotation even when the first motor element (2) has not caused the movement.

The articulation (1) object of the present invention prevents the presence of additional torque measurement elements in the articulation (1) as it takes advantage of the various functionalities of the structural components that can simultaneously be used as sensors.

The articulation (1) object of the invention performs a force measurement of one of the components of $F_n$, this component being the one that is given by the resistive force of the resistive element (11) ($F_{thrust}$). In FIG. 5, the geometric relations that allow obtaining the resistive force $F_n$ as a function of the "vertical" component, i.e. as a function of $F_{thrust}$ can be seen.

The graduated scale (10) and the linear measurement element (9) allow knowing the compression (C) of the resistive element (11) and the velocity when knowing the time at which this compression occurs (velocity=change in the position/time).

So, knowing the intrinsic characteristics of the resistive element (11) (mainly the constants "K" and "A" of the elements that make up this resistive element (11)) and the values measured by the measurement elements (9, 17), it is possible to know the reactive force on the second device (22).

Once knowing the pre-compression of the resistive element (11), i.e. the displacement (D) that the thrust element (15) moved by the spindle (16) associated to the second motor (12) has experienced, the linear measurement element (9) gives the reading of the displacement experienced by the transmission rod (7) in the deflection of the articulation (1) (coincident with the compression (C) of the resistive element (11)), and the resistive force of the resistive element ($F_{thrust}$) is obtained from:

$$F_{thrust} = K \cdot C + A \cdot \text{Vel}$$

To know the torque developed by the articulation, it is necessary to know the value of $F_n$, where $F_n$ is the force of contact between the surfaces of the frame (4) and of the wheel (8) in the radial direction of the wheel (8).

$$\text{Torque} = \vec{b} \times \vec{F}_n$$

Force $\vec{F}_n$ can be decomposed into:
a perpendicular force supported by the structure ($F_{structure}$) and
the reaction force of the resistive element (11) ($F_{thrust}$) in the compression direction.

$$Fn = F_{thrust} \cos(\varphi)$$

$$\varphi = \arccos\left[\frac{\overline{b}^2 + \overline{OA}^2 - r^2}{2 \cdot \overline{b} \cdot \overline{OA}}\right]$$

$\overline{b}$, the vector that represents an "arm" distance between the articulation rotation axis (O) and the point of contact of the frame (4) with the wheel (8) is known from the relation, (see FIG. 5)

$$\overline{b} = \sqrt{\overline{OB}^2 + R^2 - 2 \cdot \overline{OB} \cdot R \cdot \cos(\beta)}$$

where (see FIG. 4),
$\overline{OB}$, is the distance from the articulation rotation axis (O) to the centre of curvature of the frame (B);
$\overline{OA}$ is the distance from the articulation rotation axis (O) to the centre of the wheel (A), which is a function of the compression of the resistive element (11);
$\overline{BA}$, is the distance from the centre of the curvature of the frame (B) to the centre of the wheel (A).
β is the complementary angle which defines the inclination of the contact force vector With equation 2, the expression of the complementary angle p that defines the inclination of the contact force vector is obtained (see FIG. 4):

$$\beta = \overline{OA} \cdot \frac{\sin\theta}{\overline{BA}}$$

θ is the angle of deflection, which is calculated according to the formula;

$$\theta = \text{acos}\left[\frac{\overline{OB}^2 + \overline{OA}^2 - \overline{BA}^2}{2\overline{OB} \cdot \overline{OA}}\right]$$

The measurement of the torque generated is obtained, as already mentioned, by the relation:

$$\text{Torque} = \vec{b} \times \vec{F}_n$$

$$\text{Torque} = \overline{b} \cdot F_n \cdot \sin(\varphi^*)$$

where $\varphi^*$ is the angle between the vectors of arm and force, which is given by the expression:

$$\varphi^* = \beta + \varphi + \theta$$

As already mentioned, using the linear measurement element (9) and the graduated scale (10) the compression (C) of the resistive element (11) is known. Furthermore, the movement of the thrust element (15) is also restricted by the transmission rod (7), which moves within the through-holes (21).

The invention discloses an articulation (1), which is actuated with controllable stiffness, and a compact force measuring device, which has a compact arrangement of elements in order to reduce the volume of the articulation (1) and which takes advantage of the resistive element (11) associated to its stiffness to provide a measure of the torque generated.

The invention should not be limited to the particular mode for carrying out the invention described in this document. Those skilled in the art can develop other modes for carrying out the invention in view of the description made herein. Accordingly, the scope of the invention is defined by the following claims.

The invention claimed is:

1. An articulation (1) with controllable stiffness, comprising:
   a first device (20) comprising a frame (4) connected to a first motor element (2), this first device (20) being configured to regulate a position of the articulation (1),
   a second device (22) configured to regulate a stiffness of the articulation (1) and which anchors the first device (20) to the articulation (1), the second device (22) comprising:
   a resistive element (11),
   a transmission rod (7) having one end attached to the resistive element (11) and an opposite end comprising a wheel (8),
   a thrust element (15) with a threaded spindle (16) through it, on which the resistive element (11) rests,
   a second motor (12) attached to the spindle (16), which provides a displacement (D) to the thrust element (15) by a rotation of said spindle (16), and
   a coupling body (13) on which the resistive element (11), the transmission rod (7), the thrust element (16), and the second motor (12) are arranged,
   wherein the displacement D of the thrust element (15) determines a pre-compression of the resistive element (11), thus determining the articulation (1) stiffness, and the first motor element (2) provides a rotation to the frame (4) of the first device, wherein the frame (4) has a curved face, such that, with the rotation of the frame (4), the wheel (8) of the second device (22) rolls on the curved face of the frame (4), and the transmission rod (7) associated with said wheel (8) causes a compression (C) of the resistive element (11) of the second device (22), thus the compression (C) and the velocity at which it occurs determines a force $F_{thrust}$ developed by the resistive element (11).

2. The articulation (1) with controllable stiffness, according to claim 1, wherein the resistive element (11) comprises an elastic element with a characteristic constant K, and/or a shock absorber element with a characteristic constant A, or a combination thereof.

3. The articulation (1) with controllable stiffness, according to claim 1, wherein the second device (21) comprises a rotational measuring element (17) connected to the second motor (12), said rotational measuring element (17) counting the revolutions of a shaft of the second motor (12) such that the displacement (D) of the thrust element (15) can be determined by performing a conversion of the revolutions of the second motor (12) and of the pitch of the spindle (16), where a revolution of the second motor (12) is equivalent to the pitch of the spindle (16) in the linear displacement of the thrust element (15) associated with the spindle (16), so that the displacement (D) of the thrust element (15) can be determined by the relation D=Revolutions·Pitch.

4. The articulation (1) with controllable stiffness, according to claim 3, wherein the second device (22) comprises a linear measurement element (9) and a graduated scale (10) attached to the transmission rod (7), such that compression experienced by the resistive element (11), and the velocity at which it occurs, associated to the rotation of the frame (4) can be determined through the linear measurement element (9), which measures the displacement of the transmission rod (7) on the graduated scale (7).

5. The articulation (1) with controllable stiffness, according claim 1, wherein the resistive element (11) associated with its stiffness may be used to obtain the measure of a torque generated at the articulation (1) by the relation:

$$\text{Torque} = \vec{b} \times \vec{F}_n, \text{ which is converted into Torque} = \overline{b} \cdot F_n \cdot \sin(\varphi^*)$$

where
   b is a vector that represents a distance between an articulation rotation axis (O) and a point of contact of the frame (4) with the wheel (8), and
   $F_n$ is the contact force between the surfaces of the frame (4) and of the wheel (8) in the radial direction of the wheel (8);
   $\varphi^*$ is an angle between the vector $\vec{b}$ and the vector $F_n$, where
   $\overline{b}$ is obtained from the relation: $\hat{b} = \sqrt{\overline{OB}^2 + R^2 - 2 \cdot \overline{OB} \cdot R \cdot \cos(\beta)}$ where $\beta$ is the complementary angle which defines the inclination of the vector of the contact force $\vec{F}_n$, and is obtained by the relation $$\beta = \overline{OA} \cdot \frac{\sin\theta}{\overline{BA}},$$

where $\theta$ is the deflection angle obtained from $$\theta = \mathrm{acos}\left[\frac{\overline{OB}^2 + \overline{OA}^2 - \overline{BA}^2}{2\overline{OB} \cdot \overline{OA}}\right],$$

where:
   $\overline{OB}$: distance from the rotation axis of the articulation (1) to the centre of curvature of the frame (B);
   $\overline{OA}$: distance from the articulation rotation axis (O) to the centre of the wheel (A);
   $\overline{BA}$: distance from the centre of the curvature of the frame (B) to the centre of the wheel (A),
   $\varphi^*$ is obtained from the expression $\varphi^* = \beta + \varphi + \theta$, where $$\varphi = \arccos\left[\frac{\overline{b}^2 + \overline{OA}^{2-r^2}}{2\cdot \overline{b}\cdot \overline{OA}}\right]$$

$$Fn = F_{thrust}\cos(\varphi)$$

where:

$$F_{thrust} = K\cdot C + A\cdot \text{Vel}$$

where K and A are the constant characteristic of the resistive element (11), C is the compression of the resistive element (11) and Vel is the velocity at which such compression occurs in the resistive element (11).

6. The articulation (1) with controllable stiffness according to claim 1, wherein the first device (20) comprises, in addition to the frame (4) and the first motor element (2):

a reducer (3) having an stationary part and an outlet part, the frame (4) being connected to the stationary part of the reducer (3), a first disc (6) connected to the reducer output (3), and a second disk (5), connected to the frame (4), into which the first disc (6) is inserted.

7. The articulation (1) with controllable stiffness, according to claim 1, wherein the coupling body (13) of the second device (22) comprises guide channels (14) that guide the movement of the thrust element (15) and through-holes (21), with the transmission rod (7) passing through the through-holes (21).

8. The articulation (1) with controllable stiffness, according to claim 1, wherein the thrust element (15) is a flat piece, whose movement is limited by the guide channels (14) of the coupling body (13) of the second device (22).

\* \* \* \* \*